(12) United States Patent
Hall et al.

(10) Patent No.: US 10,191,044 B2
(45) Date of Patent: Jan. 29, 2019

(54) FLUSHABLE TEST STRIP (71) Applicants: David R. Hall, Provo, UT (US); Dan Allen, Springville, UT (US)

(72) Inventors: David R. Hall, Provo, UT (US); Dan Allen, Springville, UT (US)

( * ) Notice: Subject to any disclaimer, the term of this patent is extended or adjusted under 35 U.S.C. 154(b) by 284 days.

(21) Appl. No.: 15/398,052

(22) Filed: Jan. 4, 2017

(65) Prior Publication Data

US 2018/0188247 A1 Jul. 5, 2018

(51) Int. Cl.
*G01N 33/543* (2006.01)

(52) U.S. Cl.
CPC .............. *G01N 33/54386* (2013.01)

(58) Field of Classification Search
None
See application file for complete search history.

(56) References Cited

U.S. PATENT DOCUMENTS

| | | | | |
|---|---|---|---|---|
| 2008/0299005 A1* | 12/2008 | Meathrel | ............... | A61K 9/006 422/552 |
| 2009/0142781 A1* | 6/2009 | Shimizu | ............... | G01N 21/76 435/7.92 |
| 2012/0135509 A1* | 5/2012 | Hall | ............... | C12Q 1/001 435/287.1 |
| 2016/0327553 A1* | 11/2016 | Edwards | ............... | G01N 33/493 |

* cited by examiner

*Primary Examiner* — Rebecca L Martinez (57) ABSTRACT

We disclose a novel diagnostic test strip which may be used to conduct biochemical assays for analytes in liquid samples. The disclosed test strip may be loaded with much smaller volumes of sample than traditional test strips. The disclosed test strip may be loaded with a precision dispenser instead of submersing the test strip into a larger volume of liquid sample. In addition, the disclosed test strip dissolves in aqueous fluid so it may be flushed into the sewer system. Consequently, it is not necessary to dispose of the disclosed test strip in biological waste containers.

20 Claims, 7 Drawing Sheets

FLUSHABLE TEST STRIP

BACKGROUND

Field of the Invention

This invention relates to test strips for conducting analytical assays, typically for medical use.

Background of the Invention

Biochemical assays using test strips for analysis of urine, blood, saliva, feces, and other biological material are often performed in a bathroom. Even when not performed in a bathroom, the test strip represents biohazard waste that must be disposed of using specific protocols. Disposal of the biowaste through the sewage system, which is suited to handle biowaste, would alleviate having to provide a separate solid waste stream.

Traditional test strips are designed to be immersed into a liquid sample or saturated by a urine stream rather than receive small volume samples through a dispenser. Consequently, they do not dissolve in the presence of aqueous solution, such as toilet water, and may not be disposed of by flushing. They typically include a layer of plastic of other hydrophobic material which will not break up in the sewer system. One purpose of the hydrophobic material is to keep the different reagents that are present on test trips from mixing when the test strip is exposed to a liquid sample. Particularly when test strips include reagents for detecting multiple analytes along the length of the test strip, the plastic keeps the test strip from absorbing the sample and drawing the different reagents along the test strip by capillary action.

Plastics or other hydrophobic material used to prevent reagent mixture on test strips are not suited for processing in the sewer system. While some plastics are biodegradable, the time scale for disintegration (for example, the INDA and EDANA standards for dispersion time) may be challenging for robust plastics. A test strip that disintegrates rapidly in water without mixing the reagents on a multi-analyte test strip is needed.

BRIEF SUMMARY OF THE INVENTION

We disclose a novel diagnostic test strip which dissolves in aqueous fluid. Consequently, the test strip may be flushed into the sewer system rather than being disposed of with biological waste. The test strip may include a substrate layer that provides rigidity to the test strip and which may be water-soluble or water-dispersible. Sections of reagent paper may be positioned along the test strip creating reagent pads. Each reagent pad may include a different reagent which participates in a chemical reaction in the presence of a specific analyte. The reagent in each reagent pad may react with a different analyte. The product of the chemical reaction may be detectable through methods such as colorimetric or fluorescent spectrometry.

A thin hydrophobic coating may be positioned between the reagent pads and the substrate layer to inhibit sample from leaking from the reagent pads into the substrate layer and causing the substrate layer to dissolve. However, the hydrophobic coating is much more thin that traditional test strips and may disperse and biodegrade in the sewer system.

Two or more sides of the reagent pads may have beveled cuts which create a trapezoidal- or parallelogram-shaped cross-section from two or more sides. The beveled cut results in sides that are angled toward the center of the strip and have more exposed cut fibers than would be present after a traditional vertical cut. These features may cause the liquid sample to absorb into the reagent pad more quickly than it would if the cuts were vertical cuts. Consequently, sample does not pool and leak into areas of the test strip that would disintegrate or result in cross-contamination of the different reagents.

After chemical reactions that may have occurred on the reagent pads are detected, the test strip may be flushed in a toilet into the sewer system. The substrate layer may dissolve upon contact with water. The reagent pads, may be mechanically disintegrated and dispersed because they may comprise paper and partially because of their small size relative to traditional test strips. The hydrophobic coating may be so thin that it is susceptible to mechanical destruction and dispersal. When the hydrophobic coating is broken into smaller particles, the surface areas of the particles are further exposed and, are therefore, susceptible to biodegradation. With the components of the disclosed test strip dissolved, dispersed, and subject to biodegradation, there may be little or no recognizable remainder of the test strip in the sewer waste stream.

DETAILED DESCRIPTION OF THE INVENTION

Definitions

Vertical, as used herein with regard to the disclosed test strip, means the plane that runs from the top to the bottom of the test strip when the test strip lays flat on a surface with the short side and long side parallel to the surface.

Horizontal, as used herein with regard to the disclosed test strip, means the plane that is parallel to the width of the test strip when the test strip lays flat on a surface with the short side and long side parallel to the surface.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Disclosed herein is a novel test strip which may be used to conduct biochemical analysis of analytes in bodily fluids. The disclosed test strip is designed to receive fluid by precision dispensing apparatuses. Consequently, the disclosed test strip requires smaller amounts of fluid than traditional test strips which are designed to be dipped into or saturated with a sample of fluid. In fact, the disclosed test strip may not be dipped into a fluid sample because it dissolves when submerged in liquid. Consequently, the disclosed test strip may be flushed in a toilet where it may be properly disposed of through a sewer system.

The disclosed test strip may include a long side and a short side (a length and a width) with multiple layers. The test strip may include a substrate layer which may be water-soluble or water-dispersible. In some embodiments, the substrate includes methyl cellulose paper which dissolves rapidly in water. In some embodiments, the thickness of the substrate layer may be between approximately 5 mils and approximately 20 mils. Some embodiments include a substrate layer that is between approximately 10 mils and approximately 16 mils. The thickness of the substrate layer may provide rigidity that may be useful when pulling the test strip through a dispenser or analytical apparatus. In some embodiments, the substrate layer may include carboxymethyl cellulose paper.

The test strip may also include sections of reagent paper which form reagent pads. The test strips may be constructed by laying strips of different reagent papers on a sheet of substrate, turning the sheet 90-degrees, then cutting strips from the sheet, each with a reagent pad which comprises a small section of each of the different reagent papers. The reagent pads may include a liquid absorbent layer that may be positioned adjacent to the substrate layer. The reagent pads may each include a reagent that may undergo a chemical reaction in the presence of a specific analyte. The chemical reaction may convert the reagent into a reaction product of a different color than the reagent. Consequently, the reagent pads may undergo a color change when exposed to fluids that include the specific analyte. The reagent pads of each strip may contain multiple reagent pads that each react to a different analyte. Therefore, each test strip may conduct multiple assays, each for a different analyte. The absorbent layer is also known as "enzyme paper" although it does not always include an enzyme.

It is relevant that the components in reagent pads on traditional test strips is limited to substrates that can be immersed. The disclosed test strip does not have this requirement. Rather, microliter amounts of liquid sample may be applied to the disclosed test strip using precision dispensing methods.

One side of the reagent pads may be coated with a thin hydrophobic coating. The hydrophobic coating may be positioned between the reagent pads and the substrate layer. The hydrophobic coating prevents liquid sample from passing from the reagent pad into the water-soluble or water-dispersible substrate layer. However, when the test strip is dropped in water, for example, into the water in a toilet bowl, the substrate layer rapidly dissolves or disperses. The thin hydrophobic coating is then susceptible to biodegradation along its large surface area. The hydrophobic coating is so thin that it is also quite susceptible to mechanical destruction and dispersal. When the hydrophobic coating is broken into smaller particles, the surface areas of the particles are further exposed and, therefore, more susceptible to biodegradation.

In some embodiments, the thin hydrophobic coating is applied by lamination techniques. In other printed using methods known in the art including, but not limited to, laser or inkjet printing. In some embodiments, the density of the hydrophobic coating may vary between segments of the test strip. Varied density may be accomplished during printing by applying grey scale printing. The varied density may cause the segments to dissolve into smaller sections more readily when exposed to water.

In some embodiments, the hydrophobic coating is continuous across the area of the test strip. Other embodiments, include gaps in the hydrophobic coating. These gaps may be between each section of reagent paper and separate the sections that include different reagents. Alternatively, some embodiments may include perforations in the test strip between the sections of reagent paper. These features may help the test strip disperse in the sewer system.

With the substrate layer and the hydrophobic coating dissolved and dispersed, the reagent pads may then dissolve, disintegrate, and disperse. The small size of the reagent pads facilitates their dispersal relative to larger sections in traditional test strips. For example, in some embodiments, each reagent pad may be approximately 5 $mm^2$ in area or smaller. At this point, there may be little or no recognizable remainder of the test strip in the sewer waste stream.

Traditional test strips are cut from panels by pressing a vertical blade down onto the panels. This method results in a square or rectangle cross section on all sides of the reagent pad. In contrast, angled blades may cut the panels during manufacture of the disclosed test strip resulting in twin beveled cuts. Two of the four sides of each reagent pad may be slanted relative to a vertical axis. In some embodiments, the cross-section of reagent paper may be trapezoidal in shape with the wider side of the trapezoid nearest the substrate layer and the shorter side of the trapezoid on the top of the test strip. In other embodiments, the cross-section of the reagent paper may approximate a parallelogram. In some embodiments, the beveled cuts may be parallel to the long side of the test strip while in other embodiment, the beveled cuts may be parallel to the short side of the test strip.

One advantage of the beveled cuts is that the reagent pads have more exposed cut paper fibers. While the surface of reagent paper may be somewhat hydrophobic, the cut fibers draw in fluid by capillary action. Consequently, while a drop of liquid placed on the top of the reagent pad may be repelled by the reagent paper and resistant to absorption, the reagent pad may be loaded from a cut side using a precision dispenser. The exposed fibers more rapidly absorb the liquid than the uncut surface of the reagent pad. Another advantage of the beveled cut is that the reagent pads are less likely to conduct fluid to the water-soluble or water-dispersible substrate layer. This is at least because the tilted wall of the reagent paper is more accessible to fluids than the straight vertical side found in traditional test strips. Therefore, the substrate layer does not contact fluid or dissolve until flushed in a toilet or dropped in other liquid for disposal.

In some embodiments, the reagent paper may be diced with a beveled cut on both sides before the strips of reagent paper are applied to the substrate layer to create a panel. Then the panels may be turned 90 degrees and diced with beveled edges resulting in a trapezoidal or parallelogram shape when viewing the test strip from both the short side and the long side. This method of dicing may create sections of reagent paper which are shaped like pyramids which are truncated at the tops. This configuration improves liquid capture from a dispenser. Sample may be dispensed onto the sloped sides rather than the top of the reagent paper which may be somewhat hydrophobic. The four inwardly sloped sides further aid in keeping the sample from reaching lower layers of the test strip and from pooling between sections of different types of reagent paper. This reduces the likelihood that different reagents will leak together between the different sections of reagent paper.

In some embodiments, the cross-section across the short end of the strip of reagent paper may be the shape of a parallelogram. In this embodiment, one side or the cross-section may be sloped up and opposite edge has an overhang. The parallelogram cross-section of this embodiment also includes a tilted side of the reagent paper which is more accessible to fluid relative to the straight vertical side found in traditional test strips.

Some embodiments of the disclosed test strip include a second hydrophobic coating. This coating may be constructed from the same materials as the thin hydrophobic coating that may be placed between the reagent paper and the substrate. Alternatively, the two hydrophobic coatings may include different materials. In some embodiments, either or both hydrophobic coating may include a biodegradable polymer. In some embodiments, either or both hydrophobic coating may include polylactic acid, poly(lactic-co-glycolic acid), or both polylactic acid and poly(lactic-co-glycolic acid).

Some embodiments of the test strip include a lateral chromatography region. The lateral chromatography region may have the same width as the reagent pads but a greater length. A fluid sample may be loaded at a sample absorption region of the lateral chromatography region. The sample absorption region may be located at one of the short ends of the lateral chromatography region. The sample may travel along the length of the lateral chromatography region by capillary action into an analyte separation region. In some embodiments, prior to traveling through the analyte separation region, the sample may be exposed to antibodies that specifically bind to certain analytes and which are conjugated with a molecule that is either colored or has a fluorescent tag. Antibodies to the analytes may also be immobilized at different regions along the length of the sample absorption region. When analytes in the sample that are already bound to the conjugated antibodies then bind to the immobilized antibodies, the signal for that analyte is detectable by detecting the conjugated molecule. Other types of lateral chromatography assays, including competitive immunoassays, are also known in the art and may be included in the disclosed test strip.

Figure 1A:
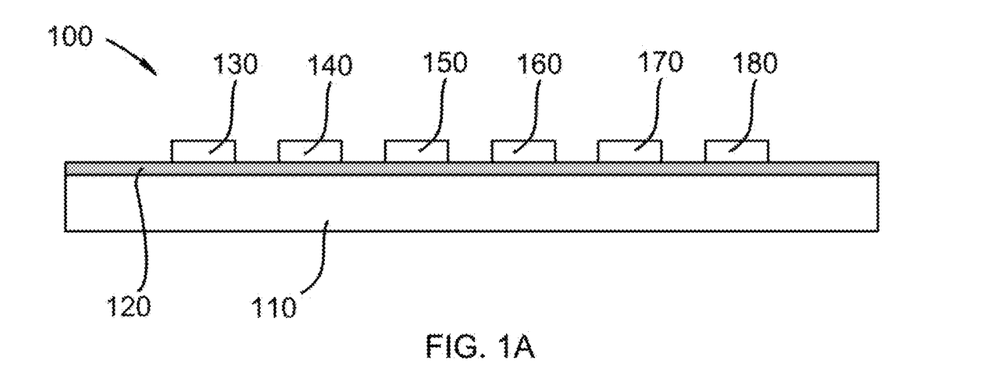
FIG. 1A is a side view of an embodiment of the disclosed test strip from the long side of the test strip.

Referring now to the drawings, FIG. 1A illustrates test strip 100, which is an embodiment of the disclosed test strip. Test strip 100 includes substrate layer 110 and reaction pads 130, 140, 150, 160, 170, and 180. Hydrophobic coating 120 is between substrate layer 110 and reaction pads 130, 140, 150, 160, 170, and 180. In test strip 100, each of the reaction pads 130, 140, 150, 160, 170, and 180 includes a different reagent that reacts in the presence of a different analyte. The reaction pads may be created by laying multiple strips of reagent paper, each including a different reagent, on a panel of substrate. The panel may then be sliced across each of the reagent strips to create multiple test strips, each with a section of the multiple reagent papers.

Figure 1B:
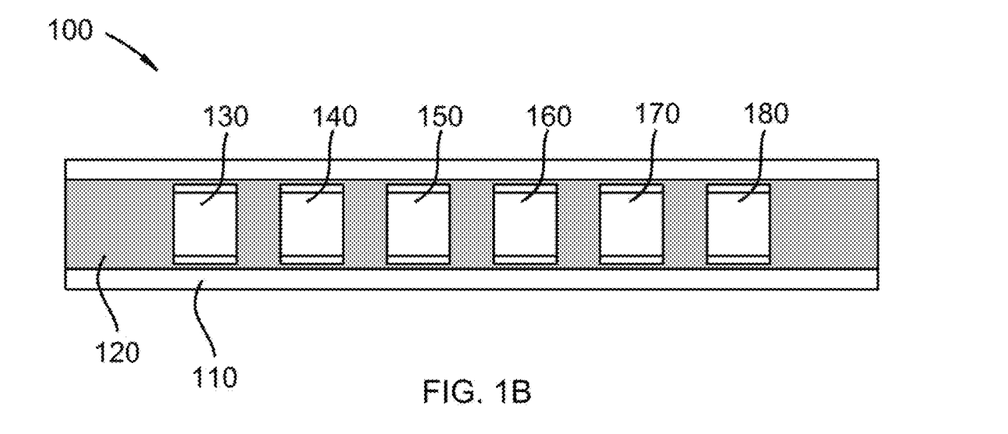
FIG. 1B is an aerial view of the test strip of FIG. 1A.

FIG. 1B is an aerial view of test strip 100. Reaction pads 130, 140, 150, 160, 170, and 180 are visible as well as parts of hydrophobic coating 120 which runs continuously beneath and between reaction pads 130, 140, 150, 160, 170, and 180 and above substrate layer 110.

Figure 1C:
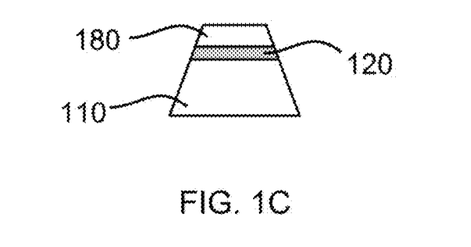
FIG. 1C is a side view of the test strip of FIGS. 1A and 1B from the short side of the test strip.

FIG. 1C is a side view of test strip 100 which is a 90-degree rotation of test strip 100 as shown in FIG. 1A. Reagent pad 180 is shown above hydrophobic coating 120 and substrate layer 110. The beveled sides of test strip 100 are shown in this view which create a trapezoidal cross section. The sides of reaction pads 130, 140, 150, 160, 170, and 180 along the long side are angled toward the center of test strip 100 (away from the plane of the paper in the drawing). In some embodiments, the long side of test strip 100 may be moved along a dispenser and the bevel-cut sides may absorb liquid as test strip 100 moves along. Liquid sample is more readily absorbed through the sides due to the angle of the cut, the trapezoidal shape, and the exposed cut paper fibers.

Figure 2A:
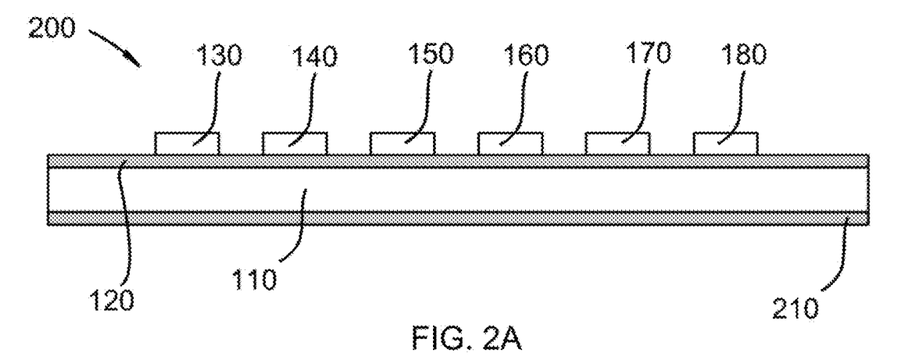
FIG. 2A is a side view from the long side of another embodiment of the disclosed test strip which includes a second hydrophobic coating.

FIG. 2A illustrates test strip 200, which is another embodiment of the disclosed test strip. Test strip 100 includes substrate layer 110, hydrophobic coating 120, and reaction pads 130, 140, 150, 160, 170, and 180. Test strip 200 further includes second hydrophobic coating 210 below substrate layer 110. Consequently, test strip 200 includes two hydrophobic coatings, one on each side of substrate layer 110, which prevent liquid from seeping into undesirable areas of test strip 100.

Figure 2B:
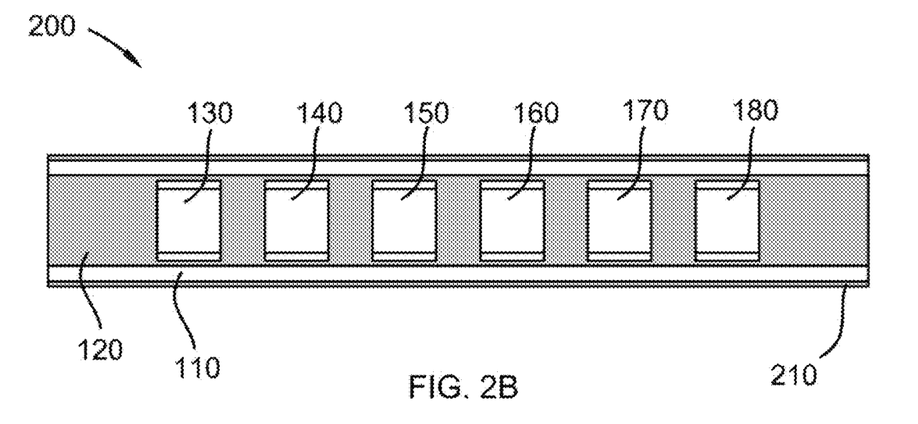
FIG. 2B is an aerial view of the test strip of FIG. 2A.

FIG. 2B is an aerial view of test strip 200. From this view, test strip 200 looks much like test strip 100. However, for illustration purposes, an edge of second hydrophobic coating 210 is shown.

Figure 2C:
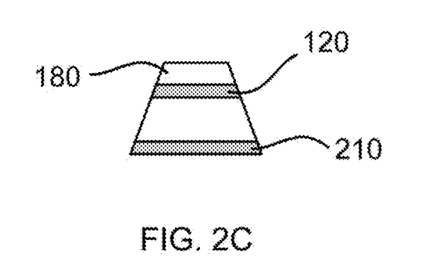
FIG. 2C is a side view of the test strip of FIGS. 2A and 2B from the short side of the test strip.

FIG. 2C is a side view of test strip 200 which is a 90-degree rotation of test strip 200 as shown in FIG. 2A. The beveled sides of reagent pad 180 are shown which function as discussed with regard to FIG. 1C. Second hydrophobic coating 210 is shown below substrate layer 120.

Figure 3A:
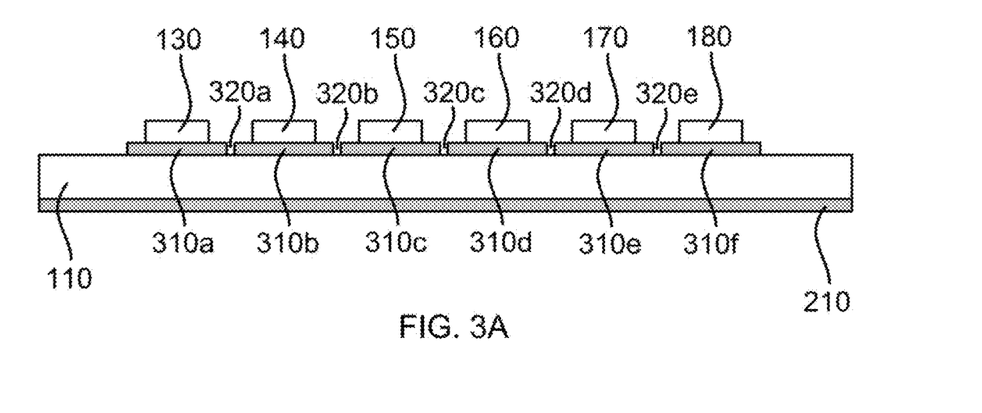
FIG. 3A is a side view from the long side of another embodiment of the disclosed test strip which includes a discontinuous hydrophobic coating.

FIG. 3A illustrates test strip 300, which is another embodiment of the disclosed test strip. Test strip 300 includes substrate layer 110, second hydrophobic coating 210, and reaction pads 130, 140, 150, 160, 170, and 180. Second hydrophobic coating 210 is continuous. However, unlike test strips 100 and 200, the hydrophobic coating between substrate layer 110 and reaction pads 130, 140, 150, 160, 170, and 180 is segmented. Hydrophobic coating sections 310a, 310b, 310c, 310d, 310e, and 310f, are beneath reaction pads 130, 140, 150, 160, 170, and 180 respectively. Gaps 320a, 320b, 320c, 320d, and 320e are between hydrophobic coating sections 310a, 310b, 310c, 310d, 310e, and 310f. This configuration may be constructed by coating the back of the reagent papers with hydrophobic coating and cutting the reagent papers into strips before laying the strips across a substrate layer. Then the sheet may be sliced across each of the reagent strips, creating a beveled cut, to produce multiple test strips with gaps 320a, 320b, 320c, 320d, and 320e between hydrophobic coating sections 310a, 310b, 310c, 310d, 310e, and 310f.

Figure 3B:
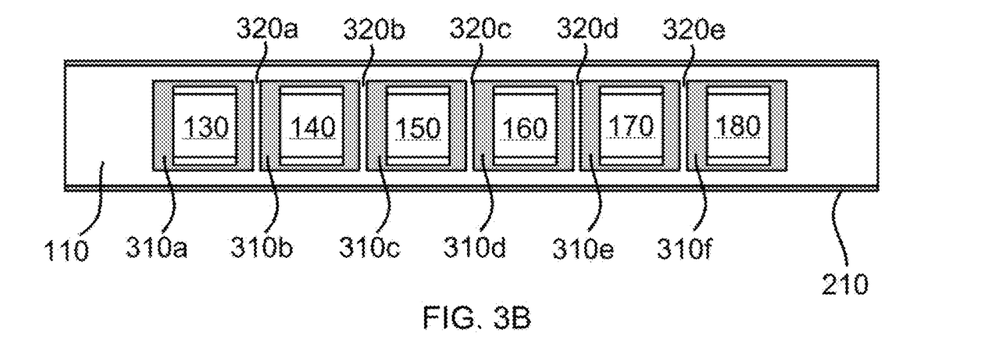
FIG. 3B is an aerial view of the test strip of FIG. 3A.

FIG. 3B is an aerial view of test strip 300. Gaps 320a, 320b 320c, 320d, and 320e are visible between hydrophobic coating sections 310a, 310b 310c, 310d, 310e, and 310f in this view.

Figure 3C:
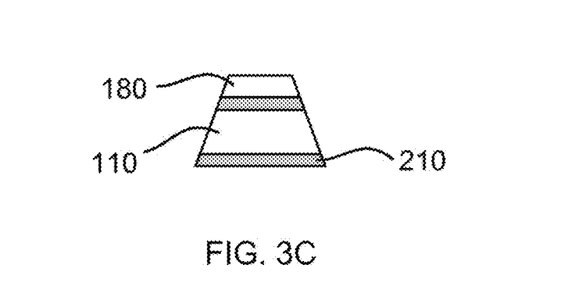
FIG. 3C is a side view of the test strip of FIGS. 3A and 3B from the short side of the test strip.

FIG. 3C is a side view of test strip 300 which is a 90-degree rotation of test strip 300 as shown in FIG. 3A. The beveled sides of reagent pad 180 are shown which function as discussed with regard to FIG. 1C. Second hydrophobic coating 210 is shown below substrate layer 120. From this view, test strip 300 is indistinguishable from the view of test strip 200 shown in FIG. 2C.

Figure 4A:
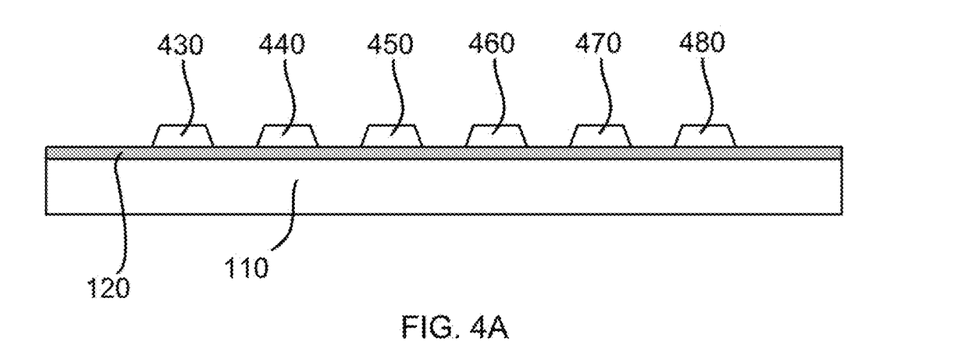
FIG. 4A is a side view from the long side of another embodiment of the disclosed test strip which includes beveled cuts on sides of the reagent pads that are opposite to those of FIGS. 1A, 2A, and 3A.

FIG. 4A illustrates test strip 400, which is another embodiment of the disclosed test strip. Test strip 400 includes substrate layer 110 and hydrophobic coating 120. In this embodiment, reagent pads 430, 440, 450, 460, 470, and 480 have trapezoidal-shaped cross-sections. This configuration may be constructed by cutting the reagent paper with a beveled cut before arranging the reagent paper on a sheet of substrate layer. The sheet may then be cut with a vertical cut so that the trapezoidal-shape is seen from the long side instead of from the short side as in test strips 100, 200, and 300. A dispenser may allocate a small volume of liquid sample between the reagent pads on the sloped portion, instead of on the top of the reagent pads or along the long side of the test strip, so that the liquid contacts the beveled side of each reagent pad. Consequently, the drop may be absorbed directly into the reagent pads.

Figure 4B:
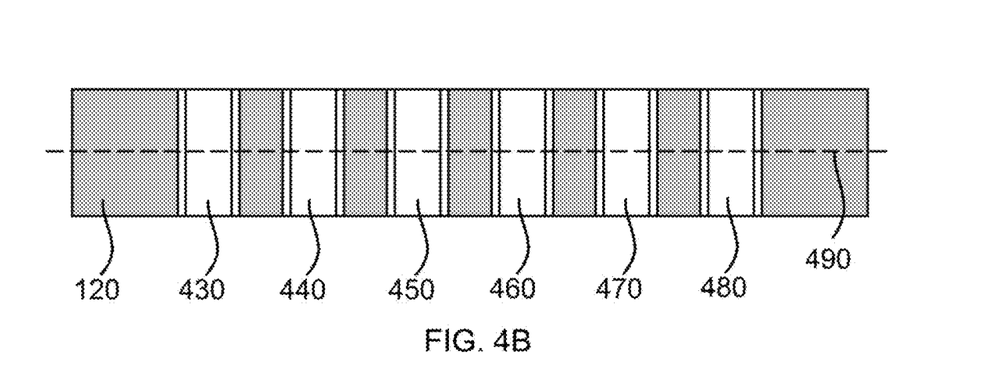
FIG. 4B is an aerial view of the test strip of FIG. 4A illustrating how a sheet may be diced into strips to construct test strips

FIG. 4B is an aerial view of test strip 400. Beveled sides of reagents pads 430, 440, 450, 460, 470, and 480 are shown. Dotted line 490 illustrates the line where the vertical cut may be made along a sheet to construct multiple test strips, each with one of reagents pads 430, 440, 450, 460, 470, and 480.

Figure 4C:
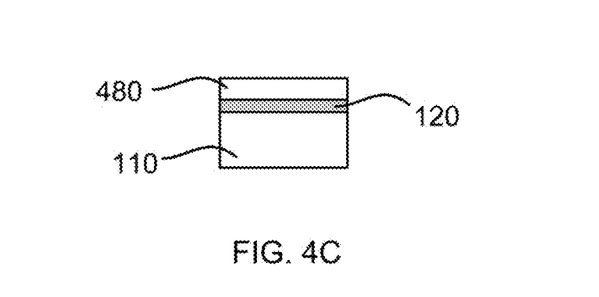
FIG. 4C is a side view of the test strip of FIGS. 4A and 4B from the short side of the test strip.

FIG. 4C is a side view of test strip 400 which is a 90-degree rotation of test strip 400 as shown in FIG. 4A. The vertical cut side of reagent pad 180 is shown which is rectangular in shape, instead of trapezoidal as in test strips 100, 200, and 300. Second hydrophobic coating 210 is shown below substrate layer 120.

Figure 5A:
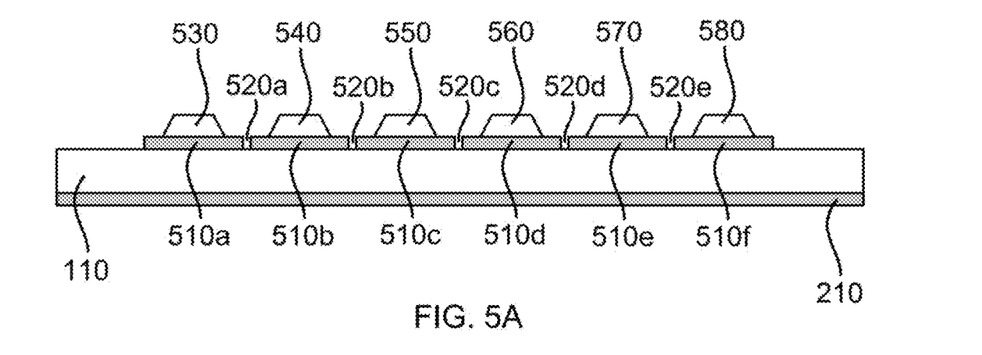
FIG. 5A is a side view from the long side of another embodiment of the disclosed test strip which includes beveled cuts on four sides of the reagent pads.

FIG. 5A illustrates test strip 500, which is another embodiment of the disclosed test strip. Test strip 500 includes substrate layer 110 and second hydrophobic layer 210. Similar to test strip 300, test strip 500 includes a discontinuous hydrophobic layer between reagent pads 530, 540, 550, 560, 570, and 580. This creates gaps 520a, 520b, 520c, 520d, and 520e between hydrophobic coating sections 510a, 510b 510c, 510d, 510e, and 510f. In addition, the reagent paper used to construct test strip 500 is cut with a beveled cut on both sides then, after the strips of reagent paper are arranged on the sheet of substrate, the test strips are cut off the sheet with beveled cuts. This causes reagent pads 530, 540, 550, 560, 570, and 580 to have beveled cuts on four sides. In this embodiment, reagent pads 530, 540, 550, 560, 570, and 580 have trapezoid-shaped sides on four sides. This results in each reagent pad having the shape of a pyramid that has been truncated at the top to remove the point.

Figure 5B:
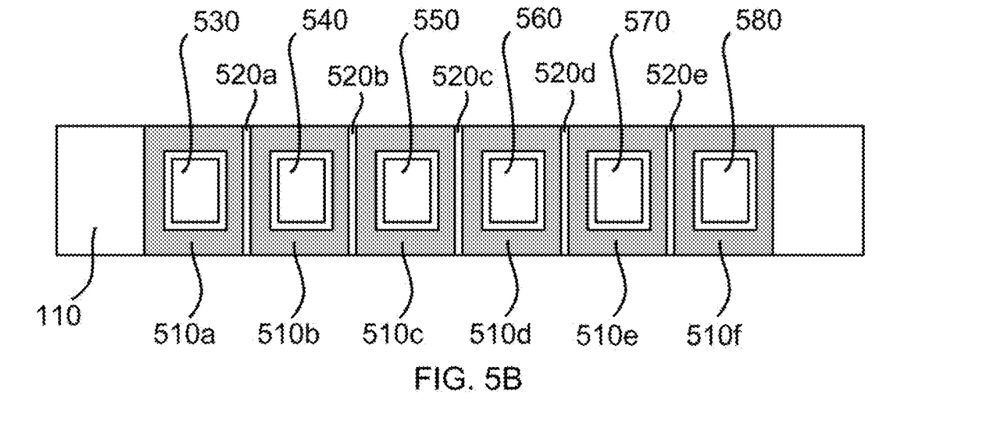
FIG. 5B is an aerial view of the test strip of FIG. 5A.

FIG. 5B is an aerial view of test strip 500. Four beveled sides of reagents pads 530, 540, 550, 560, 570, and 580 are shown. The top of a truncated pyramid is shown.

Figure 5C:
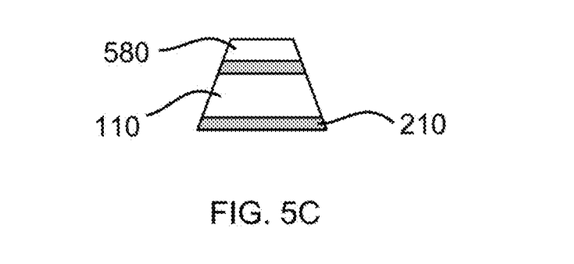
FIG. 5C is a side view of the test strip of FIGS. 5A and 5B from the short side of the test strip.

FIG. 5C is a side view of test strip 500 which is a 90-degree rotation of test strip 500 as shown in FIG. 5A. The trapezoidal side of reagent pad 580 is illustrated.

Figure 6A:
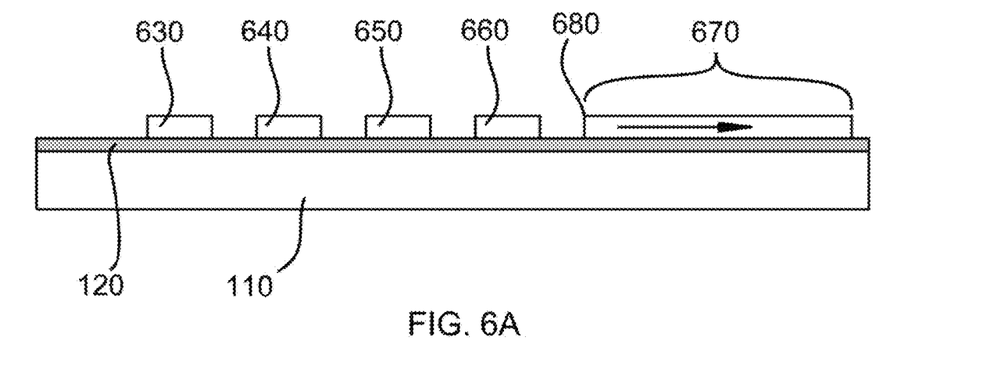
FIG. 6A is a side view from the long side of another embodiment of the disclosed test strip which includes a lateral chromatography region.

FIG. 6A illustrates test strip 600, which is another embodiment of the disclosed test strip. Test strip 600 includes substrate layer 110 and hydrophobic layer 120. Reagent pads 630, 640, 650, and 660, are shown. In addition, test strip 600 includes lateral chromatography region 670. A liquid sample is loaded at sample loading region 680. The liquid moves along lateral chromatography region 670 in the direction illustrate by the arrow, which is through and analyte separation region.

Figure 6B:
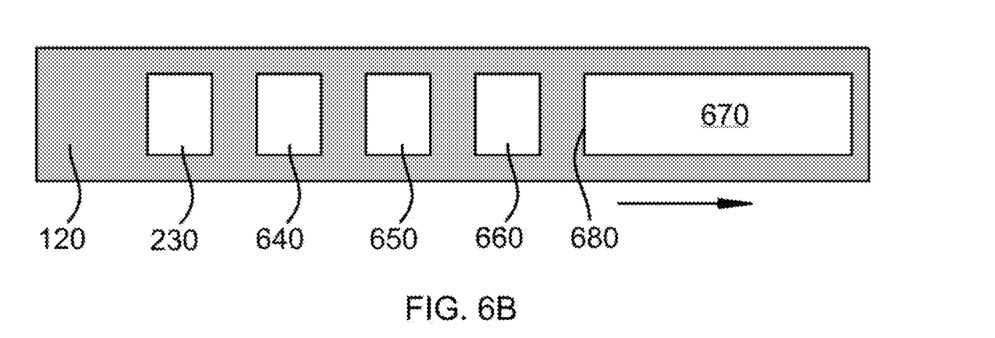
FIG. 6B is an aerial view of the test strip of FIG. 6A.

FIG. 6B is an aerial view of test strip 600. Again, the arrow illustrates the direction sample moves through lateral chromatography region 670 after being loaded at sample loading region 680.

Figure 6C:
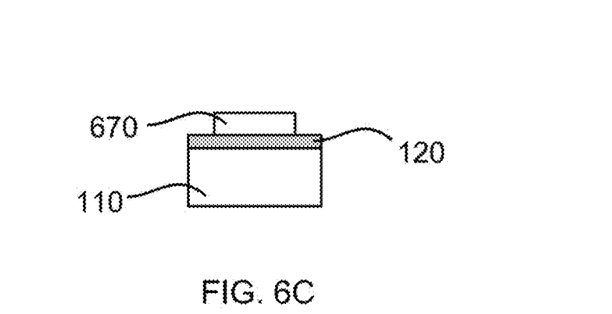
FIG. 6C is a side view of the test strip of FIGS. 6A and 6B from the short side of the test strip.

FIG. 6C is a side view of test strip 600 which is a 90-degree rotation of test strip 600 as shown in FIG. 6A. A short side of lateral chromatography region 670 is visible above hydrophobic coating 120 and substrate layer 110.

Figure 7:
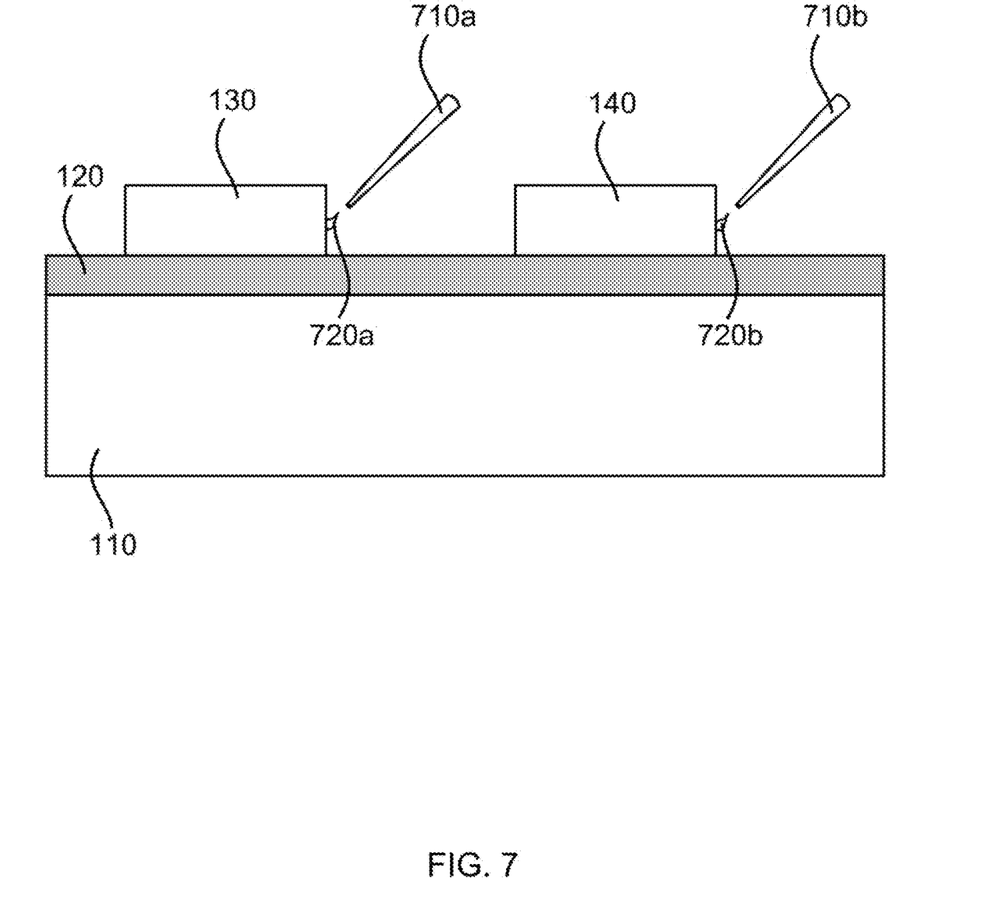
FIG. 7 is a section of the test strip of FIGS. 1A, 1B, and 1C illustrating how it may be loaded with sample.

FIG. 7 shows a section of test strip 100 being loaded with sample. As illustrated in FIGS. 1A and 1B, test strip 100 includes substrate layer 110, hydrophobic layer 120, and reagent pads 130 and 140. Two micro-dispensers, dispenser 710a and dispenser 710b, are shown loading reagent pads 130 and 140 respectively with samples 720a and 720b. Samples 720a and 720b may be aliquots of sample from the same source. Samples 720a and 720b are loaded on the beveled cut sides of reagent pads 130 and 140, which has exposed cut paper fibers and is angled away from dispensers 710a and 710b. These sides of reagent pads 130 and 140 absorb samples 720a and 720b respectively much more quickly than if samples 720a and 720b had been dispensed onto the top of reagent pads 130 and 140, which may be somewhat hydrophobic. The beveled cut sides of reagent pads 130 and 140 may absorb samples 720a and 720b before they leak elsewhere on test strip 100.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A diagnostic test strip comprising:
   a length and a width, wherein the length is greater than the width;
   a substrate layer, wherein the substrate layer comprises a material that is water-soluble or water-dispersible;
   a first hydrophobic coating; and
   a plurality of reaction pads wherein each of the plurality of reaction pads comprises a reagent that participates in a chemical reaction in the presence of an analyte, wherein each of the plurality of reaction pads comprise a liquid absorbent material, and wherein the first hydrophobic coating is between the first side of the substrate layer and the plurality of reaction pads,
   wherein a vertical cross-section of the reaction pads comprises at least two sides that are slanted relative to a vertical axis.

2. The diagnostic test strip of claim 1, wherein the vertical cross-section is parallel to the width of the diagnostic test strip and is approximately trapezoidal in shape.

3. The diagnostic test strip of claim 2, wherein a vertical cross-section is parallel to the length of the diagnostic test strip and is approximately trapezoidal in shape.

4. The diagnostic test strip of claim 1, wherein the vertical cross-section of the reaction pads is parallel to the width of the diagnostic test strip and is approximately a parallelogram.

5. The diagnostic test strip of claim 1, wherein the vertical cross-section of the reaction pads is parallel to the length of the diagnostic test strip and is approximately a parallelogram.

6. The diagnostic test strip of claim 4, wherein the thickness of the substrate is between approximately 5 mils and approximately 20 mils.

7. The diagnostic test strip of claim 4, wherein the thickness of the substrate is between approximately 10 mils and approximately 16 mils.

8. The diagnostic test strip of claim 1, wherein a horizontal cross-section of each of the plurality of reaction pads is approximately 5 $mm^2$.

9. The diagnostic test strip of claim 1, wherein the first hydrophobic coating is continuous over the substrate layer.

10. The diagnostic test strip of claim 1, wherein the first hydrophobic coating is discontinuous and wherein the first hydrophobic coating comprises a gap between each of the plurality of reaction pads.

11. The diagnostic test strip of claim 1, wherein density of the hydrophobic coating varies along the length of the diagnostic test strip.

12. The diagnostic test strip of claim 1, further comprising a second hydrophobic coating, wherein the second hydrophobic coating is adjacent to a second side of the substrate layer, wherein the second side of the substrate layer is opposite the first side of the substrate layer.

13. The diagnostic test strip of claim 12, wherein at least one of the first hydrophobic coating and the second hydrophobic coating comprises a biodegradable polymer.

14. The diagnostic test strip of claim 13, wherein the biodegradable polymer is selected from one or more of the following: polylactic acid and poly(lactic-co-glycolic acid).

15. The diagnostic test strip of claim 1, wherein the chemical reaction results in a change in either the colorimetric or fluorescent spectra of the reagent.

16. The diagnostic test strip of claim 1, wherein the substrate layer comprises carboxymethyl cellulose paper.

17. The diagnostic test strip of claim 1, further comprising lateral chromatography region, the lateral chromatography region comprising: a sample loading region and an analyte separation region, wherein the sample loading region is laterally offset from the analyte separation region, wherein the sample loading region is in fluid communication with the analyte separation region, wherein the sample loading region comprises a liquid absorbent material, and a vertical cross-section that comprises at least two sides that are slanted relative to a vertical axis.

18. The diagnostic test strip of claim 17, wherein the lateral chromatography region further comprises antibodies, wherein the antibodies adhere to a specific analyte.

19. The diagnostic test strip of claim 1, wherein at least one of the plurality of reaction pads comprises an enzyme.

20. The diagnostic test strip of claim 1, further including a plurality of perforations between the plurality of reaction pads.

\* \* \* \* \*